United States Patent [19]

Robins et al.

[11] 4,246,408
[45] Jan. 20, 1981

[54] IMIDAZO[1,2-A]-S-TRIAZINE

[75] Inventors: Roland K. Robins; Ganapathi R. Revankar, both of Provo, Utah

[73] Assignee: ICN Pharmaceuticals, Covina, Calif.

[21] Appl. No.: 18,797

[22] Filed: Mar. 8, 1979

[51] Int. Cl.$^3$ ............... C07D 403/00; C07D 251/18
[52] U.S. Cl. .................................. 544/209; 536/24; 544/204
[58] Field of Search ............... 536/24; 544/204, 209, 544/212

[56] References Cited

U.S. PATENT DOCUMENTS 3,454,559  7/1969  Yamazaki et al. ............... 536/24

OTHER PUBLICATIONS

Kim, S., et al., J. Med. Chem., vol. 21, 883, 1978.
Prisbe, E., et al., J. Org. Chem., vol. 43, 4774–4784, 1978.
Prisbe, E., et al., J. Org. Chem., vol. 43, 4785–4794, 1978.

Primary Examiner—Johnnie R. Brown
Assistant Examiner—Blondel Hazel
Attorney, Agent, or Firm—K. H. Boswell

[57] ABSTRACT

Imidazo[1,2-a]-s-triazines including the base, the nucleoside, derivatives of the nucleoside, and the 5' nucleotide are prepared and are useful as antiviral Agents against RNA viruses.

1 Claim, No Drawings

IMIDAZO[1,2-A]-S-TRIAZINE

BACKGROUND OF THE INVENTION

Certain imidazo[1,2-a]-s-triazines including the base, the nucleoside, and the nucleotide are prepared and have been tested and found to be biologically active as an antiviral agent for RNA type viruses.

Over the last three decades medical science has discovered and learned to use chemotherapeutic agents having activity against microorganisms including bacterium and certain fungi. Excluded from this group have been agents which are active against viruses. In the last few years research has been centered on finding effective chemotherapeutic antiviral agents. At present there are only a very few compounds known to be active against viruses.

In search of biologically active compounds, scientists have realized and have been able to understand in great detail the function of many of the biological pathways active within living organisms. With this understanding has come the realization that certain synthetic compounds might be designed which will mimic naturally occurring compounds in respect to their ability to interact with appropriate binding sites on enzymes and other important biological constituents. Many derivatives of naturally occurring compounds such as nucleosides and nucleotides have been prepared but only a select few have expressed the necessary biological activity.

The imidazo[1,2-a]-s-triazine ring system is related to the naturally occurring purine ring system in that certain of the nitrogen atoms in the ring system of the above noted triazine ring are placed in positions which correspond to the same positions in the purine ring. While many different ring systems have been prepared in attempts to mimic the biological activity of the purine ring system the imidazo [1,2-a]-s-triazine ring system has not until very recently been prepared. The compounds of the present invention have an amino group and a keto group in what corresponds to the 2 and 6 positions, respectively, of the purine ring. As such they are related to the purine guanine. Guanine itself is not active as an antiviral agent but is found as its nucleotide in both RNA and DNA.

Recently we published a paper describing the preparation of the instant system in the *Journal of Medicinal Chemistry,* 1978, Volume 21, number 9, 883, the entire disclosure of which is herein incorporated by reference. Additionally, two other papers have appeared in the literature describing this ring system. These papers are both by Prisbe et al, in *The Journal of Organic Chemistry,* Volume 43, No. 25, 1978, 4774 and 4784.

SUMMARY OF THE INVENTION

The imidazo[1,2-a]-s-triazine ring system may be regarded as a 5-aza-7-deazapurine. The present invention is directed to the base, nucleoside, blocked nucleosides and the nucleotide of the 2-amino-4-hydroxy derivatives of the imidazo[1,2-a]-s-triazine ring system.

The group of compounds are compounds of the structure:

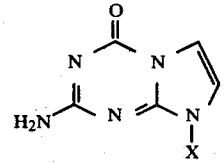

wherein X is H,β-D-ribofuranosyl,β-D-ribofuranosyl 5-phosphate, $C_1$–$C_{18}$ acyl β-D-ribofuranosyl and 2,3-isopropylidene-β-D-ribofuranosyl.

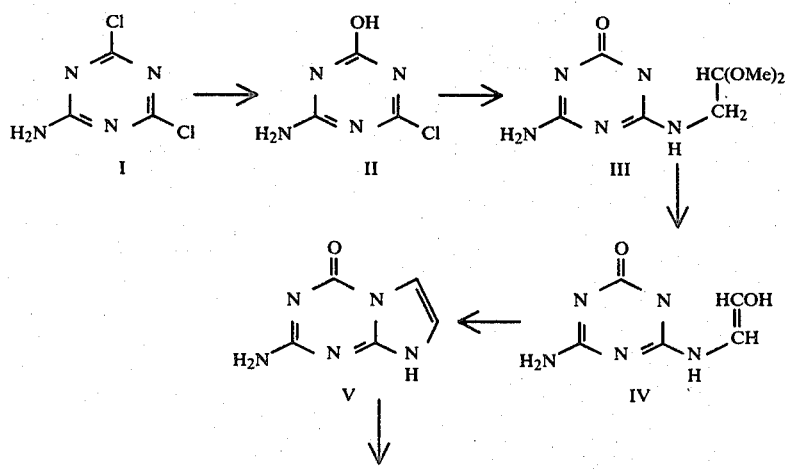

-continued

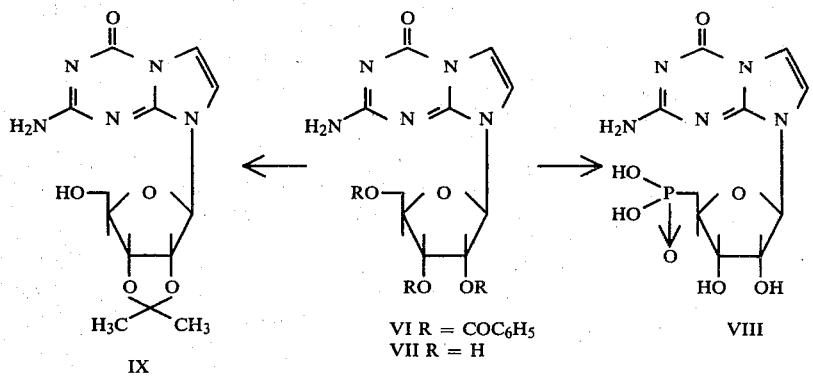

VI R = COC₆H₅
VII R = H

2-Amino-4-chloro-6-hydroxy-s-triazine (hereinafter referred to as COMPOUND II) is described in *Chem. Abst.*, 77, 165133y (1972). This compound in turn can be prepared from 2-amino-4,6-dichloro-s-triazine (hereinafter referred to as COMPOUND I) by controlled hydrolysis of one of the halogens of COMPOUND I. Condensation of COMPOUND II with aminoacetaldehyde dimethyl acetal in aqueous basic media at reflux temperatures gave crystalline 2-amino-4-(2,2-dimethoxyethylamino)-s-triazin-6-one (hereinafter referred to as COMPOUND III) in a good yield. Hydrolysis of the acetal groups of COMPOUND III was achieved by heating COMPOUND III in 6 N hydrochloric acid on a steambath under a nitrogen atmosphere to give the hydrochloride salt of 2-amino-4(2-hydroxyvinyleneamino)-s-triazin-4-one. The free-base of this compound, hereinafter referred to as COMPOUND IV, was obtained by careful neutralization of an aqueous solution of the hydrochloride salt. Ring annulation of either COMPOUND IV or its hydrochloride salt in concentrated sulfuric acid at 95° C. for 1.5 hours gave crystalline 2-aminoimidazo[1,2-a]-s-triazin-4-one (hereinafter referred to as COMPOUND V) in a good yield.

Compound V was glycosylated by treatment with hexamethyldisilazane in the presence of ammonium sulfate to give a gummy bis(trimethylsilyl) derivative which was then treated with 1-O-acetyl-2,3,5-tri-O-benzoyl-β-D-ribofuranose in anhydrous 1,2-dichloroethane containing stannic chloride at room temperature. After purification a good yield of 2-amino-8-(2,3,5-tri-O-benzoyl-β-D-ribofuranosyl)imidazo[1,2-a]-s-triazin-4-one (hereinafter referred to as COMPOUND VI) was obtained. COMPOUND VI was obtained as a chromatographically pure homogeneous foam. COMPOUND VI was debenzolylated with methanolic sodium methoxide at ambient temperature to yield 2-amino-8-(β-D-ribofuranosyl)imidazo[1,2-a]-s-triazin-4-one (hereinafter referred to as COMPOUND VI.

The structure of COMPOUNDS V and VII was established NMR spectroscopy using both proton and carbon-13 NMR as described in our *Journal of Medicinal Chemistry* paper referred to above, the disclosure of which is herein incorporated by reference.

Compound VII was directly phosphorylated using phosphorus oxychloride in trimethyl phosphate at from about 0° to about 5° C. for about five hours followed by hydrolysis to yield 2-amino-8-(β-D-ribofuranosyl)imidazo[1,2-a]-s-triazin-4-one 5'-monophosphate (hereinafter referred to as COMPOUND VIII). COMPOUND VIII was isolated as a free acid after ion exchange chromatography.

COMPOUND VII was converted to its 2',3'-O-isopropylidene derivative by treatment with 70% perchloric acid and 2,2-dimethoxypropane in anhydrous acetone at room temperature to yield 2-amino-8-(2,3-O-isopropylidene-β-D-ribofuranosyl)imidazo[1,2-a]-s-triazine-4-one (hereinafter referred to as COMPOUND IX). Compound IX was used as a structure proof of the anomeric configuration of COMPOUND VII.

While the nucleotide COMPOUND VIII was isolated as the free acid it could also be prepared as an acceptable physiological salt. Acceptable salts can be selected from but are not necessarily limited to the group consisting of alkali and alkaline earths, e.g., sodium, potassium, calcium, magnesium, lithium, ammonium and substituted ammonium, trialkylammonium, dialkylammonium, alkylammonium, e.g., triethylammonium, trimethylammonium, diethylammonium octylammonium, cetyltrimethylammonium, cetylpyridium. The hydroxyl groups of the nucleoside compound VII can be blocked with $C_1$–$C_{18}$ acyl groups. These groups can be selected from a group consisting of straight chain, branched chain, substituted, unsaturated saturated or aromatic acid such as, but not necessarily limited to, acetic, trifluoroacetic, propionic, n-butyric, isobutyric, valeric, caproic, pelargonic, enanthic, capyrlic, latic, acrylic, propargylic, palmitic, benzoic, phthalic, salicyclic, cinnamic and naphthoic acids. A more preferred acyl blocking group would be $C_1$–$C_8$ acyls members of the above group.

The compounds of the instant invention demonstrate antiviral activity against RNA type viruses. This activity was detected using the cytopathic effect (CPE) as an indicator of antiviral activity. Activity was detected for the CPE effect as per the method of Sidwell, et al., *Applied Microbiology*, 22: 797–801, 1971, the disclosure of which is herein incorporated by reference and are expressed as VR (virus rating). As a control a known antiviral 1-(β-D-ribofuranoxyl)-1,2,4-triazole-3-carboxamide was simultaneously run.

DETAILED DESCRIPTION

Melting points were taken on a Thomas-Hoover capillary melting point apparatus and are uncorrected. Specific rotations were measured in a 1-dm tube with a Perkin-Elmer Model 141 automatic digital readout polarimeter. Nuclear magnetic resonance (NMR) spectra were recorded at 60 MHz on a Hitachi Perkin-Elmer R-20A spectrometer in $Me_2SO$-$d_6$ as well as in $D_2O$-NaOD using DSS as an internal standard. The presence of water as indicated by elemental analyses was verified by NMR. $^{13}C$ NMR spectra of 5% $Me_2SO$-$d_6$ solutions were obtained at 22.6 MHz with Bruker HX-90E Fourier transform spectrometer, equipped with a Bruker-Nicolet data system. Model B-NC-12. Chemical shifts were measured from $Me_2SO-d_6$ and converted to the $Me_4Si$ scale using the relationship δ $Me_4Si$=δ $Me_2SO-d_6$+39.5 ppm. Ultraviolet spectra (UV, sh=shoulder) were recorded on a Cary Model 15 spectrophotometer and infrared spectra (IR) on a Perkin-Elmer 257 spectrophotometer (KBr pellets). Elemental analyses were performed by Galbraith Laboratories, Inc., Knoxville, Tenn., and the results are within ±0.4% of the theoretical values. Thin-layer chromatography (TLC) was run on silica gel F-254 (EM Reagents) plates. ICN Woelm silica gel (70–230 mesh) was used for column chromatography. Detection of components on TLC was by ultraviolet light and with 10% sulfuric acid in methanol spray followed by heating. Evaporations were carried out under reduced pressure with the bath temperature below 30° C.

EXAMPLE 1

2-Amino-4-chloro-6-hydroxy-s-triazine II

2-Amino-4,6-dichloro-s-triazine 16.5 g, 0.1 mol) was suspended in 250 mL of water containing sodium hydroxide (4.4 g,0.11 mol), and the mixture was stirred at room temperature for 15 h. The mixture was filtered to remove 5.0 g of unreacted starting material before the cooled (0°–5° C.), clear, colorless filtrate was neutralized (pH 6.8–7.0) with glacial acetic acid. The white solid that separated was collected, washed with cold water (5×25 mL), and dried. It was crystallized from hot water to yield 7.5 g (73.4%, based on the recovery of the starting material): mp>320° C. (lit. mp 300° C.); UV$\lambda_{max}$(pH 1)225 nm ($\epsilon$=7400); UV$\lambda_{max}$ (pH 7) 250 nm ($\epsilon$=4600); UV$\lambda_{max}$(pH 11) 247 nm ($\epsilon$=3600). Anal. ($C_3H_3ClN_4O$, 146.54) C, H, N.

EXAMPLE 2

2-Amino-4-(2,2-dimethoxyethylamino)-s-triazin-6-one (III)

A suspension of 2-amino-4-chloro-6-hydroxy-s-triazine (II) 15.0 g, 0.102 mol) in 250 mL of water was treated with sodium hydroxide (4.095 g, 0.102 mol), and the mixture was stirred to obtain a clear solution which was treated with aminoacetaldehyde dimethyl acetal (12.9 g, 0.12 mol). The mixture was heated under gentle reflux for 2.5 h. with stirring and then cooled to room temperature. The crystalline solid that separated was collected and washed with cold water (2×25 mL). Recrystallization from a large excess of water gave the compound as needles: 15.0 g (68.0%); mp 285° C. dec. Anal. ($C_7H_{13}N_5O_3$, 215.21) C, H, N.

EXAMPLE 3

2-Amino-4-(2-hydroxyvinyleneamino)-s-triazin-4-one (IV)

A solution of 2-amino-4-(2.2-dimethoxyethylamino)-s-triazin-6-one (3,8.0 g, 0.037 mol) in 6 N hydrochloric acid (160 mL) was heated on a steam bath in an evaporating dish under a stream of nitrogen to dryness. The residue was coevaporated with water (2×50 mL) followed by ethanol (2×50 mL). The dry residue was triturated with cold ethanol and filtered. The residue was washed with cold ethanol (2×10 mL) followed by ether and dried to yield the dihydrochloride salt. The salt was dissolved in water (100 mL) and carefully neutralized with solid sodium bicarbonate before it was stored in the refrigerator overnight. The white solid that separated was collected and crystallized from water as needles to yield 4.9 g (78.0%): mp >310° C. (begins to discolor above 200° C.); UV$\lambda_{max}$(pH 1) 232 nm ($\epsilon$=20400); UV$\lambda_{max}$(pH 7 and 11) 234 nm ($\epsilon$=8650). Anal. ($C_5H_7N_5O_2$, 169.15) C, H, N.

EXAMPLE 4

2-Aminoimidazo[1,2-a]-s-triazin-4-one (5-Aza-7-deazaguanine V

A solution of 2-amino-4-(2-amino-4-(2-hydroxyvinylene-amino)-s-triazin-4-one (4,6.0 g, 0.035 mol) in concentrated sulfuric acid (16.0 mL) was heated at 95° C. for 1.5 h. with stirring and was poured (after cooling to room temperature) into ice-water (50 mL) containing sodium carbonate (20.0 g). The pH of the solution was adjusted to 6.5–7.0 using additional base before it was stored in the refrigerator overnight. The solid that deposited was collected, washed with cold water (3×15 mL), and then crystallized from water with the aid of Norit as tiny, off-white needles: 3.8 g (70.9%; mp >330° C.; NMR ($D_2O$-NaOD) δ 7.07 (d,J=2.0 Hz, $C_7H$), 7.34 (d,J=2.0 Hz, $C_6H$); UV$\lambda_{max}$(pH 1) 242 nm, sh ($\epsilon$=9400), 261 (13600); UV$\lambda_{max}$(pH 7) 252 nm ($\epsilon$=12000); UV$\lambda_{max}$(pH 11) 255 nm ($\epsilon$=10600). Anal. ($C_5H_5N_5O$, 151.13) C, H, N.

EXAMPLE 5

2-Amino-8-(2,3,5-tri-O-benzoyl-β-D-ribofuranosyl)imidazo[1,2-a]-s-triazin-4-one (VI)

A mixture of dry 2-aminoimidazo[1,2-a]-s-triazin-4-one (V) 3.02 g, 0.020 mol), freshly distilled hexamethyldisilazane (15.0 mL), and a few crystals of ammonium sulfate (25 mg) was heated at reflux temperature for 15 h. with the exclusion of moisture. The clear, slightly brown solution was fractionated by distillation to remove excess of hexamethyldisilazane and the residual gum was presumed to be the bis(trimethylsilyl) derivative which was used without further prification. To a solution of the above trimethylsilyl derivative in anhydrous 1,2-dichloroethane (100 mL) was added 1-O-acetyl-2,3,5-tri-O-benzoyl-β-D-ribofuranose (10.09 g, 0.02 mol) followed by stannic chloride (7.0 g, 0.027 mol). The reaction mixture was protected from moisture and stirred for 30 h. at ambient temperature. The brown reaction solution was then poured into 200 mL of chloroform, with efficient stirring and keeping the mixture basic at all times. The resulting emulsion was filtered through a Celite pad which was washed with chloroform (3×25 mL). The combined organic layer was washed with water (2×100 mL) before it was dried over anhydrous sodium sulfate. The solvent was evaporated to a light brown foam which was chromatographed on an open-bed, silica gel column (5×75 cm) prepacked in ethyl acetate and eluted with ethyl acetate-water-1-propanol (4:2:1, v/v, upper phase). The band containing the requisite product was collected and the solvent evaporated to leave 6.8 g (56.30%) of a light yellow, chromatographically homogeneous foam: $[\alpha]^{25}_D$-32.0° (cl.O.$Me_2SO$); UV$\lambda_{max}$(pH 1) 233 nm ($\epsilon$=45800), 268 (18800); UV$\lambda_{max}$(pH 7) 235 nm ($\epsilon$=39400), 263 sh (24700); UV$\lambda_{max}$(pH 11) 234 nm ($\epsilon$=42300), 260 sh (20600). Anal. ($C_{31}H_{25}N_5O_8$.0.5$H_2O$, 604.57) C, H, N.

EXAMPLE 6

2-Amino-8-(β-D-ribofuranosyl)imidazo[1,2-a]-s-triazin-4-one (VII)

Method 1

To a solution of 2-amino-8-(2,3,5-tri-O-benzoyl-β-D-ribofuranosyl)imidazo[1,2-a]-s-triazin-4-one (VI) 6.04 g, 0.01 mol) in anhydrous methanol (200 mL) was added 1 N sodium methoxide in methanol until the pH of the solution was 8.5–9.0, and the resulting solution was stirred at ambient temperature for 20 h with the exclusion of moisture. The solid that separated was collected by filtration and crystallized from water with the aid of decolorizing carbon as microneedles. The filtrate from above was neutralized with glacial acetic acid before it was evaporated to dryness. The residue was dissolved in water (100 mL) and the aqueous solution was extracted with chloroform (4×50 mL) before it was decolorized with carbon. The aqueous filtrate was concentrated to 15 mL and stored in the refrigerator overnight. The crystalline solid that deposited was collected and the combined crystals were recrystallized from water to yield 2.2 g (77.7%): mp 251°–252° C. dec; $[\alpha]^{25}_D -25.9°$ (c1.0, H$_2$O); NMR (Me$_2$SO-d$_6$) δ 5.85 (d,J=5.0 Hz,C$_1$H), 7.0 (br s, NH$_2$), 7.47 (d,J=2.0 Hz, C$_7$H), 7.55 (d,J=2.0 Hz, C$_6$H), and other sugar protons; UVλ$_{max}$(pH 1) 238 nm, sh (ε=8800), 264 (14700); UVλ$_{max}$(pH 7) 210 nm (ε=28800, 256 (13800); UVλ$_{max}$(pH 11) 217 nm (ε=4700), 256 (13800; IR 1620 (C=O) of heterocycle), 3360 cm$^{-1}$ (NH$_2$). Anal. (C$_{10}$H$_{13}$N$_5$O$_5$, 283.24) C, N.

Method 2

2-Acetamido-8-(2,3,5-tri-O-benzoyl-β-D-ribofuranosyl)imidazo[1,2-a]-s-triazin-4-one (16, 3.18 g, 0.005 mol) was treated with 1 N sodium methoxide in a similar fashion to that described in method 1 above to give 1.25 g (88.3%) of a product with identical melting point and IR, NMR, UV, TLC, and elemental analyses as that obtained in method 1.

EXAMPLE 7

2-Amino-8-(2,3-O-isopropylidene-β-D-ribofuranosyl)imidazo[1,2-a]-s-triazin-4-one (IX)

2,2-Dimethoxypropane (2.0 mL) and 70% perchloric acid (2.0 mL) were added to dry acetone (400 mL). The mixture was protected from moisture and stirred at room temperature for 5 min before 2-amino-8-(β-D-ribofuranosyl)imidazo[1,2-a]-s-triazin-4-one (VII, 1.42 g, 0.005 mol) was added in one portion. The mixture was stirred for 3 h and pyridine (2.0 mL) was added. The volume was reduced to about 25 mL; 10% aqueous sodium carbonate solution (40 mL) was added before the remaining acetone was removed. Cold water (20 mL) was added to the aqueous solution which was then left at 5° C. overnight. The crystals that deposited were collected and recrystallized from aqueous ethanol as needles to yield 1.1 g (67.8%): mp 222°–224° C.; NMR (Me$_2$SO-d$_6$).β1.34 (s,CH$_3$), 1.53(s,CH$_3$), 5.95 (d,J=2.5 Hz, C$_1$H), 7.03 (br s, NH$_2$) 7.41 (d, J=2.0 Hz, C$_7$H), 7.52 (d, J=2.0 Hz, C$_6$H), and other sugar protons; UVλ$_{max}$ (pH 1) 237 nm, sh (ε=7100), 265 (11600); UVλ$_{max}$ (pH 7) 210 nm (ε=22300), 256 (10600); UVλ$_{max}$ (pH 11) 216 nm (ε=2300), 255 (11000). Anal. (C$_{13}$H$_{17}$N$_5$O$_5$, 323.21) C, H, N.

EXAMPLE 8

2-Amino-8-(β-D-ribofuranosyl)imidazo[1,2-a]-s-triazin-4-one 5'-Monophosphate VIII)

Redistilled phosphorus oxychloride (1.0 g) and trimethyl phosphate (10.0 mL) were cooled to 0° C. in an ice bath. Dry 2-amino-8(β-D-ribofuranosyl)imidazo[1,2-a]-s-triazin-4-one (VII, 1.0 g, 0.0035 mol) was added all at once and the mixture was stirred at 0°–5° C. until solution was complete (20 min) before it was allowed to stand in the refrigerator (3°–4° C.) for 4.5 h with occasional agitation. The clear, colorless reaction mixture was poured into ice-water (50 mL) containing sodium carbonate (1.5 g) with efficient stirring and external cooling. The mixture was occasionally stirred in the ice bath for 1 h and the pH was monitored at 5–6 by adding sodium carbonate when needed. The pH-stabilized solution was extracted with ether (2×50 mL) and the aqueous phase was concentrated in vacuo until salts began to crystallize. Enough water was added to complete solution; the pH was adjusted to 6–7 and then applied to a column containing Dowex 1-X2 (100–200 mesh, formate form, 50 mL). The resin was washed with water (2.5 L) to remove unreacted VII and the inorganic salts. The compound was obtained by gradient elution (0.1 M formic acid to water). The eluent containing the compound was pooled, concentrated to about 50 mL, frozen, and lyophilized to yield 0.42 g of the 5'-monophosphate which was slightly impure on TLC (silica gel, 2-propanol-concentrated ammonium hydroxide-water, 7:1:2, v/v). The impure phosphate was dissolved in water (10 mL) and passed through a column containing fresh formate resin (50 mL). It was eluted as above to yield 0.37 g (27.5%) of analytically pure VIII as an amorphous powder after workup as above: mp 205° C. dec; $[\alpha]^{25}_D$-19.0° (c 1.0, H$_2$O), NMR (Me$_2$SO-d$_6$) δ 5.85 (d,J=5.5 Hz, C$_1$H), 7.05 (br s, NH$_2$), 7.41 (d,j=2.4 Hz, C$_7$H), 7.58 (d,J=2.5 Hz, C$_6$H), and other sugar protons; UVλ$_{max}$ (pH 1) 239 nm, sh (ε=7150), 265 (11650); UVλ$_{max}$ (pH 7) 211 nm (22150), 257 (10900); UVλ$_{max}$ (pH 11) 257 nm (ε=10900). Anal. (C$_{10}$H$_{14}$N$_5$O$_8$P.H$_2$O, 381.23) C, H, N.

EXAMPLE 9

Antiviral Evaluation

Inhibition of the virus-induced cytopathic effect (CPE) was used as the indicator of antiviral activity. CPE was observed in human carcinoma of the nasopharynx (KB) cells after infection with the test virus. In this system, monolayers (19–24 h) of cells were exposed to 320 CCID$_{50}$ of virus and concentrations of each compound ranging in one-half log dilutions from 1000 to 1 g/mL were added within 15 min. The degree of CPE inhibition and compound cytotixicity were observed microscopically after 72 h of incubation at 37° C. and scored numerically in order to calculate a virus rating (VR). Significance of antiviral activity in terms of VR's has been assigned as follows: 0.5, slight or no activity; 0.5–0.9, moderate activity; and ≧1.0, marked activity. The results were run in parallel with 1-(β-D-ribofuranosyl)-1,2,4-trizole-3-carboximide as a control. 2-Aminoimidazo [1,2-a]-s-triazin-4-one V and 2-amino-8-(β-C-ribofuranosyl)imidazo[1,2-a]-s-triazin-4-one VII had approximately equal, moderate antiviral activity against five rhino viruses, comparable with the control compound. Slight antiviral activity was observed with 2-amino-8-(β-D-ribofuranosyl)imidazo[1,2-a]-s-triazin-4-one 5'-monophosphate VIII. Compounds V and VII had marked activity against vesicular stomatitis virus, coxsackie B-1 virus and Echo-6 virus.

We claim:
1. 2-aminoimidazo[1,2-a]-s-triazin-4-one.

* * * * *